United States Patent
Kroll

(10) Patent No.: US 6,180,412 B1
(45) Date of Patent: Jan. 30, 2001

(54) TEST FOR CHLORINE IN WATER

(75) Inventor: Dan J. Kroll, Fort Collins, CO (US)

(73) Assignee: Hach Company, Loveland, CO (US)

(*) Notice: Under 35 U.S.C. 154(b), the term of this patent shall be extended for 0 days.

(21) Appl. No.: 09/276,956

(22) Filed: Mar. 26, 1999

(51) Int. Cl.[7] .......................... G01N 33/00; G01N 33/18
(52) U.S. Cl. ........................ 436/125; 422/61; 436/102; 436/119; 436/124; 436/127; 436/135; 436/166
(58) Field of Search .............................. 422/61; 436/102, 436/100, 119, 124, 125, 127, 166, 175, 135

(56) References Cited

U.S. PATENT DOCUMENTS 4,409,182 * 10/1983 Macklem ................................ 422/61
5,362,650 * 11/1994 Harp ...................................... 436/125

FOREIGN PATENT DOCUMENTS 61-218942 * 9/1986 (JP).

OTHER PUBLICATIONS

M. H. Mariano Anal. Chem. Sep. 1968, 40, 1662–1667.*
G. Gordon et al, Talanta Feb. 1991, 39, 145–149.*
D. W. Emerson Microchem. J. 1994, 50, 116–124, Sep. 1968.*

* cited by examiner

Primary Examiner—Arlen Soderquist
(74) Attorney, Agent, or Firm—Dean P. Edmundson

(57) ABSTRACT

An improved test is described for chlorine in pool and spa water where potassium monopersulfate is used as an oxidizing agent and DPD is used as an indicator. N,N-bis(hydroxyethyl)-2-aminoethane sulfonic acid or bicine is used to mask or eliminate the potassium monopersulfate so that it does not interfere with the DPD indicator. The test is very reliable and accurate.

5 Claims, No Drawings

US 6,180,412 B1

TEST FOR CHLORINE IN WATER

FIELD OF THE INVENTION

This invention relates to chlorine testing in pool and spa water. More particularly, this invention relates to removing interference caused by the presence of potassium monopersulfate in the water.

BACKGROUND OF THE INVENTION

Pool and spa water must be treated periodically (e.g., at two-week intervals or whenever cloudiness is present) to increase the clarity of the water and reduce eye burn and chlorine odor by destroying monochloramine which may be present in the water. A commonly-used agent for this purpose is Oxone® (i.e., potassium monopersulfate) which is a strong oxidizing agent. It is commonly used as an auxiliary oxidant (i.e. shocking agent) in swimming pools and spas to reduce the organic content of the water.

Unlike chlorine-based shocking agents that superchlorinate the water, the use of potassium monopersulfate does not increase the chlorine level in the water. Consequently, a pool does not have to be closed except for a short period of time to fully circulate the agent.

Because the potassium monopersulfate is not a disinfectant, it must be used in conjunction with a chlorine or bromine-based disinfectant. This use of chlorine in addition to the potassium monopersulfate, however, causes a problem. Because a pool or spa is usually opened shortly after the addition of the agent, it is necessary to test the levels of chlorine or bromine that are present. Unfortunately, the potassium monopersulfate in the water interferes with DPD, the most common test for these disinfectants.

The DPD (N,N-diethyl-p-phenylenediamine) method for determining free and total chlorine in water and wastewater has been widely used for many years. The DPD amine is oxidized by chlorine to two oxidation products. At a near neutral pH, the primary oxidation product is a semi-quinoid cationic compound known as a Wurster dye. This relatively stable free radical species accounts for the magenta color in the DPD colorimetric test. DPD can be further oxidized to a relatively unstable, colorless imine compound. When DPD reacts with small amounts of chlorine at a near neutral pH, the Wurster dye is the principal oxidation product. At higher oxidant levels, the formation of the unstable colorless imine is favored-resulting in apparent "fading" of the colored solution. The DPD Wurster dye color has been measured photo-metrically at wavelengths ranging from 490 to 555 nanometers (nm).

Monochloramine and dichloramine are slow to react directly with DPD at a near neutral pH. To quantify these species, the test is performed under slightly acidic conditions in the presence of iodide ion. The iodide reacts with the chloramines to form iodine as the triiodide ion ($I_3^-$). The triiodide, in turn, reacts with DPD, forming the Wurster oxidation product.

Although potassium monopersulfate interference with a free chlorine test is only slight, it produces significant interference with a total chlorine test. The total chlorine test relies on the ability of combined chlorine to convert iodide to iodine which then reacts with DPD to form a colored product. Potassium monopersulfate is also capable of making this conversion and, at a use rate of approximately 30 ppm, the interference is severe. A water sample containing no chlorine and 30 ppm potassium monopersulfate will typically produce a false reading of 5 ppm chlorine.

Previous attempts to eliminate potassium monopersulfate have involved the addition of EDTA (ethylenediaminetetraacetic acid). However, when EDTA is combined with the DPD, its ability to mask the monopersulfate is diminished. If additional EDTA is added, it is not soluble in a DPD solution (which must be stored at a very low pH to maintain stability). Only a limited amount, 0.5% by weight, of EDTA is soluble in a low pH DPD solution. This small amount of EDTA is not sufficient to eliminate the monopersulfate before it can react with the DPD.

There has not heretofore been provided a reliable test for chlorine in water (such as pool and spa water) when using potassium monopersulfate as an oxidizing agent.

SUMMARY OF THE INVENTION

In accordance with the present invention, there is provided an improved test for chlorine (and bromine) in a water sample when using DPD (i.e., N,N-diethyl-p-phenylenediamine) as an indicator and potassium monopersulfate as an oxidizing agent. The improvement involves the use of a reagent to mask or eliminate the potassium monopersulfate in the water sample. Useful reagents for this purpose are N,N-bis-(hydroxyethyl)-2-aminoethane sulfonic acid (sometimes referred to as BES) and bicine (i.e., N,N-bis(2-hydroxyethyl)glycine).

Use of one of these reagents in the test enables the DPD to effectively and reliably indicate the amount of chlorine (and bromine) in the water sample. Interference from potassium monopersulfate in the test is eliminated.

Other features and advantages of the method of the invention will be apparent from the following detailed description.

DETAILED DESCRIPTION OF THE INVENTION

Preferably, the improved test for chlorine in a water sample (e.g., from a pool or spa) is conducted as follows:

1. An appropriate sample of water to be tested is collected. The preferred sample sizes are 5, 10 or 25 mL.

2. The DPD indicator is added to the sample along with a buffer to adjust the pH to near neutral. Either the BES or bicine reagent can be added to the sample immediately after the indicator, or the reagent may be incorporated into the indicator solution, if desired. The reagents may be in any form (liquid, powder, test strips, etc.). The DPD indicator will turn pink if any chlorine is present. A suitable DPD indicator solution for use in this invention, which includes BES, is as follows, for a 1 L solution:

| | |
|---|---|
| DPD | 0.1 Kg |
| BES | 0.094 Kg |
| Deionized water | Sufficient to make 1 L |

Organic or mineral acid To adjust pH to less than 2 The DPD solution may also contain a small amount of a chelating agent such as EDTA.

3. The sample is swirled to mix, and then the sample is let to stand for about 30 seconds, preferably, to allow the reagent to remove the monopersulfate. The color may be read visually using a color comparator or it may be measured with a spectrophotometer.

4. Alternatively, the sample may be titrated with a ferrous ammonium sulfate (FAS) solution until the pink color disappears. The concentration of the FAS solution isn't critical, but it is preferred to be 0.0018 N. This is equivalent to 0.1 mg/L $Cl_2$ per drop of titrant at 25 drops/mL when using a 25 mL sample.

5. The number of drops of titrant used is then multiplied by the appropriate factor to obtain the concentration of free chlorine present in the sample. In the case of a 25 mL sample and a 0.0018 N titrant, the factor would be 0.1 mg/L $Cl_2$ per drop of titrant.

6. Then a source of iodide is added which is adequate to allow all of the combined chlorine present to convert the iodide to iodine. Preferably, 5 drops of a 10% potassium iodide solution is added to be sure that the iodide is present in excess. If any combined chlorine is present, it will react with the iodide to form iodine which in turn will react with the DPD to form a pink color. The color may be read visually using a color comparator or it may be measured with a spectrophometer.

7. Alternatively, the sample may be titrated with a ferrous ammonium sulfate (FAS) solution (of the type described above) until the pink color disappears. The number of drops of titrant used is multiplied by the appropriate factor to obtain the concentration of combined chlorine present (e.g. with a 25 mL sample and a 0.0018 N titrant, the factor would be 0.1 mg/L $Cl_2$ per drop of titrant.

8. To obtain the value for total chlorine present, the value of the free chlorine is added to the value for the combined chlorine.

To demonstrate the effectiveness of the method of the invention as compared to a conventional method in which EDTA was used as a masking agent, several water samples were tested using both methods. The results are summarized in the following table, wherein absorbance was measured with a spectrophotometer at 530 nm with a 1 cm cell.

| Sample | Absorbance (DPD with 10% BES) | Absorbance (DPD with 0.5% EDTA) |
|---|---|---|
| 30 ppm monopersulfate Free chlorine test | 0.010 | 0.005 |
| 30 ppm monopersulfate Total chlorine test | 0.025 | 1.099 |
| 30 ppm monopersulfate with monochloramine Free chlorine test | 0.023 | 0.020 |
| 30 ppm monopersulfate with monochloramine Total chlorine test | 0.131 | 1.139 |
| Monochloramine No monopersulfate Total chlorine test | 0.128 | 0.121 |

This data shows that the use of BES rather than EDTA is very superior as a masking agent for potassium monopersulfate in the tests for chlorine in water.

Another aspect of the invention is a method for determining the amount of monopersulfate which may be present in a water sample. The method involves the following steps:

1. Collecting an appropriate water sample. Any size sample can be used but will change the factor by which the number of drops of titrant must be multiplied in order to obtain the appropriate answer. Preferred sample sizes are 5, 10 or 25 mL.

2. Adding to the sample a DPD indicator with iodide but without any BES present. Any oxidizers will cause the DPD to turn pink. The color may be read visually with a color comparator or it may be measured using a spectrophotometer.

3. Alternatively, the sample may be titrated with a ferrous ammonium sulfate (FAS) solution until the pink color disappears. The concentration of the FAS solution isn't critical. The preferred solution is 0.0018 N. This is equivalent to 0.1 mg/L $Cl_2$ per drop of titrant at 25 drops/mL when using a 25 mL sample.

4. The number of drops is multiplied by the appropriate factor to obtain the concentration of oxidizer (TO) as $Cl_2$ present.

5. Use the results along with the measurement of total chlorine (TC) made with BES present in the test to calculate the concentration of monopersulfate present (i.e., monopersulfate as $Cl_2 = TO_{(no\ BES\ present)} - TC_{(BES\ present)}$). To obtain the value for monopersulfate as monopersulfate, multiply the monopersulfate as $Cl_2$ reading by a factor of 5.

Other variants are possible without departing from the scope of this invention.

What is claimed is:

1. A method for preventing interference of potassium monopersulfate when testing a water sample for the presence of chlorine or bromine when using DPD as an indicator, the method comprising the step of adding an effective amount of a reagent selected from the group consisting of N,N-bis-(hydroxyethyl)-2-aminoethane sulfonic acid and bicine.

2. A method in accordance with claim 1, wherein said reagent and DPD are contained in an aqueous solution prior to being added to the water sample.

3. A method in accordance with claim 2, wherein the concentration of said reagent in said aqueous solution is in the range of about 1 to 20% by weight.

4. A method in accordance with claim 2, wherein said reagent comprises N,N-bis-(hydroxyethyl)-2-aminoethane sulfonic acid.

5. A method for determining the amount of monopersulfate that is present in a water sample comprising:

(a) adding to the sample a DPD indicator;

(b) determining total oxidizer present in said sample;

(c) determining total chlorine present in said sample using N,N,-bis-(hydroxyethyl)-2-aminoethane sulfonic acid;

(d) subtracting the total chlorine value from the total oxidizer value.

* * * * *